(12) United States Patent
Markham et al.

(10) Patent No.: US 9,610,451 B2
(45) Date of Patent: Apr. 4, 2017

(54) DIRECT INTEGRATION OF FEEDTHROUGH TO IMPLANTABLE MEDICAL DEVICE HOUSING USING A GOLD ALLOY

(71) Applicant: Heraeus Precious Metals GmbH & Co. KG, Hanau (DE)

(72) Inventors: Jacob Markham, Vadnais Heights, MN (US); Ulrich Hausch, Frankfurt (DE)

(73) Assignee: Heraeus Deutschland GmbH & Co. KG, Hanau (DE)

( * ) Notice: Subject to any disclaimer, the term of this patent is extended or adjusted under 35 U.S.C. 154(b) by 0 days.

(21) Appl. No.: 14/104,636

(22) Filed: Dec. 12, 2013

(65) Prior Publication Data

US 2015/0165218 A1    Jun. 18, 2015

(51) Int. Cl.
*A61N 1/05* (2006.01)
*B23K 1/00* (2006.01)
(Continued)

(52) U.S. Cl.
CPC .......... *A61N 1/3754* (2013.01); *B23K 1/0008* (2013.01); *B23K 1/0016* (2013.01); *B23K 1/20* (2013.01); *B23K 35/007* (2013.01); *B23K 35/0222* (2013.01); *B23K 35/0244* (2013.01); *B23K 35/0255* (2013.01);
(Continued)

(58) Field of Classification Search
CPC ........................ B23K 35/3013; B23K 2203/14
See application file for complete search history.

(56) References Cited

U.S. PATENT DOCUMENTS 3,065,533 A * 11/1962 Dungan et al. ............... 228/121
3,979,187 A    9/1976 Scherer
(Continued)

FOREIGN PATENT DOCUMENTS

DE         69729719      7/2005
DE        102006054249   5/2008
(Continued)

OTHER PUBLICATIONS

Bulletin of Alloy Phase Diagrams, 1980, vol. 1, No. 2, p. 51-53.*
(Continued)

*Primary Examiner* — Devang R Patel
(74) *Attorney, Agent, or Firm* — Dicke, Billig & Czaja, PLLC

(57) ABSTRACT

One aspect provides a method of attaching a feedthrough to a titanium housing of an implantable medical device. The method includes providing the housing with a flange forming a recess about an opening through the housing, the opening disposed within the recess. A feedthrough is positioned within the recess so as to form a gap between the flange and an insulator of the feedthrough. A braze preform is then positioned within the recess about the insulator, the braze preform comprising a biocompatible braze material having a melting point less than a β-transus temperature of the titanium of the housing. The preform is melted at a temperature less than the β-transus temperature of the titanium of the housing such that the melted braze material fills at least the gap, and then cooled to form a braze joint which bonds the insulator to the housing and hermetically seals the opening.

14 Claims, 9 Drawing Sheets

(51) Int. Cl.

| | | |
|---|---|---|
| *A61N 1/375* | (2006.01) | |
| *B23K 1/20* | (2006.01) | |
| *B23K 35/30* | (2006.01) | |
| *B23K 35/02* | (2006.01) | |
| *B23K 35/00* | (2006.01) | |
| *C21D 9/50* | (2006.01) | |
| *B23K 35/38* | (2006.01) | |
| *B23K 1/008* | (2006.01) | |
| *B23K 101/36* | (2006.01) | |
| *B23K 103/14* | (2006.01) | |

(52) U.S. Cl.
CPC .......... *B23K 35/30* (2013.01); *B23K 35/3013* (2013.01); *B23K 35/38* (2013.01); *B23K 35/383* (2013.01); *C21D 9/50* (2013.01); *B23K 1/008* (2013.01); *B23K 2201/36* (2013.01); *B23K 2203/14* (2013.01)

(56) References Cited

U.S. PATENT DOCUMENTS

| | | |
|---|---|---|
| 4,152,540 A | 5/1979 | Duncan et al. |
| 4,217,137 A | 8/1980 | Kraska et al. |
| 4,315,054 A | 2/1982 | Sack et al. |
| 4,352,951 A | 10/1982 | Kyle |
| 4,354,964 A | 10/1982 | Hing et al. |
| 4,362,792 A | 12/1982 | Bowsky et al. |
| 4,456,786 A | 6/1984 | Kyle |
| 4,488,673 A | 12/1984 | Hopper, Jr. |
| 4,602,956 A | 7/1986 | Partlow et al. |
| 4,678,868 A * | 7/1987 | Kraska et al. ........ 174/152 GM |
| 4,737,601 A | 4/1988 | Gartzke |
| 4,774,953 A | 10/1988 | Foote |
| 4,816,621 A | 3/1989 | Huebner et al. |
| 4,991,582 A | 2/1991 | Byers et al. |
| 4,992,910 A | 2/1991 | Evans |
| 5,043,535 A | 8/1991 | Lin |
| 5,046,262 A | 9/1991 | Kerbaugh |
| 5,245,999 A | 9/1993 | Dahlberg et al. |
| 5,272,283 A | 12/1993 | Kuzma |
| 5,333,095 A | 7/1994 | Stevenson et al. |
| 5,407,119 A | 4/1995 | Churchill et al. |
| 5,408,066 A | 4/1995 | Trapani et al. |
| 5,513,793 A | 5/1996 | Malmgren |
| 5,515,604 A | 5/1996 | Horine et al. |
| 5,587,111 A | 12/1996 | Watanabe et al. |
| 5,648,302 A | 7/1997 | Brow et al. |
| 5,654,106 A | 8/1997 | Purnell et al. |
| 5,683,435 A | 11/1997 | Truex et al. |
| 5,738,270 A | 4/1998 | Malmgren |
| 5,750,926 A | 5/1998 | Schulman et al. |
| 5,756,408 A | 5/1998 | Terashi et al. |
| 5,769,874 A | 6/1998 | Dahlberg |
| 5,782,891 A * | 7/1998 | Hassler et al. ................. 607/36 |
| 5,796,019 A | 8/1998 | Lupton et al. |
| 5,821,011 A | 10/1998 | Taylor et al. |
| 5,851,222 A | 12/1998 | Taylor et al. |
| 5,855,711 A | 1/1999 | Araki et al. |
| 5,861,714 A | 1/1999 | Wei et al. |
| 5,866,851 A | 2/1999 | Taylor et al. |
| 5,870,272 A * | 2/1999 | Seifried et al. ............... 361/302 |
| 5,905,627 A | 5/1999 | Brendel et al. |
| 6,031,710 A | 2/2000 | Wolf et al. |
| 6,093,476 A | 7/2000 | Horiuchi et al. |
| 6,232,004 B1 | 5/2001 | Lasater |
| 6,284,080 B1 | 9/2001 | Haq et al. |
| 6,414,835 B1 | 7/2002 | Wolf et al. |
| 6,579,492 B2 | 6/2003 | Wehler |
| 6,586,675 B1 | 7/2003 | Bealka et al. |
| 6,643,903 B2 | 11/2003 | Stevenson et al. |
| 6,660,116 B2 | 12/2003 | Wolf et al. |
| 6,999,818 B2 | 2/2006 | Stevenson et al. |
| 7,035,076 B1 | 4/2006 | Stevenson |
| 7,038,900 B2 | 5/2006 | Stevenson et al. |
| 7,068,491 B1 | 6/2006 | Burdon et al. |
| 7,107,099 B1 | 9/2006 | O'Phelan et al. |
| 7,136,273 B2 | 11/2006 | Stevenson et al. |
| 7,145,076 B2 | 12/2006 | Knappen et al. |
| 7,174,219 B2 | 2/2007 | Wahlstrand et al. |
| 7,174,223 B2 | 2/2007 | Dalton et al. |
| 7,222,419 B2 | 5/2007 | Horng et al. |
| 7,260,434 B1 | 8/2007 | Lim et al. |
| 7,274,963 B2 | 9/2007 | Spadgenske |
| 7,437,817 B2 | 10/2008 | Zhang et al. |
| 7,480,988 B2 | 1/2009 | Ok et al. |
| 7,502,217 B2 | 3/2009 | Zhao et al. |
| 7,561,917 B2 | 7/2009 | Wegrzyn, III et al. |
| 7,564,674 B2 | 7/2009 | Frysz et al. |
| 7,569,452 B2 | 8/2009 | Fu et al. |
| 7,630,768 B1 | 12/2009 | Coffed et al. |
| 7,668,597 B2 | 2/2010 | Engmark et al. |
| 7,706,124 B2 | 4/2010 | Zhao et al. |
| 7,720,538 B2 | 5/2010 | Janzig et al. |
| 7,736,191 B1 | 6/2010 | Sochor |
| 7,742,817 B2 | 6/2010 | Malinowski et al. |
| 7,747,321 B2 | 6/2010 | Fischbach et al. |
| 7,761,165 B1 | 7/2010 | He et al. |
| 7,765,005 B2 | 7/2010 | Stevenson |
| 7,794,256 B1 | 9/2010 | Sochor |
| 7,818,876 B2 | 10/2010 | Suaning |
| 7,901,761 B1 | 3/2011 | Jiang et al. |
| 7,930,032 B2 | 4/2011 | Teske et al. |
| 7,970,474 B2 | 6/2011 | Starke |
| 7,989,080 B2 | 8/2011 | Greenberg et al. |
| 8,000,804 B1 | 8/2011 | Wessendorf et al. |
| 8,065,009 B2 | 11/2011 | Biggs |
| 8,131,369 B2 | 3/2012 | Taylor et al. |
| 8,131,376 B1 | 3/2012 | Faraji et al. |
| 8,155,743 B2 | 4/2012 | Rundle et al. |
| 8,163,397 B2 | 4/2012 | Ok et al. |
| 8,179,658 B2 | 5/2012 | Brendel et al. |
| 8,189,333 B2 | 5/2012 | Foster |
| 8,288,654 B2 | 10/2012 | Taylor et al. |
| 8,346,362 B2 | 1/2013 | Kinney et al. |
| 8,355,785 B1 | 1/2013 | Hammond et al. |
| 8,391,983 B2 | 3/2013 | Lim |
| 8,494,635 B2 | 7/2013 | Troetzschel et al. |
| 8,497,435 B2 | 7/2013 | Nagata et al. |
| 8,528,201 B2 | 9/2013 | Troetzschel et al. |
| 8,552,311 B2 | 10/2013 | Koester et al. |
| 8,656,736 B2 | 2/2014 | Terao |
| 8,659,870 B2 | 2/2014 | Brendel et al. |
| 8,742,268 B2 | 6/2014 | Reisinger et al. |
| 8,755,887 B2 | 6/2014 | Troetzschel et al. |
| 8,825,162 B2 | 9/2014 | Reisinger |
| 8,886,320 B2 | 11/2014 | Troetzschel et al. |
| 8,894,914 B2 | 11/2014 | Pavlovic |
| 8,929,987 B2 | 1/2015 | Troetzschel et al. |
| 2001/0013756 A1 | 8/2001 | Mori et al. |
| 2001/0018012 A1 | 8/2001 | Harmand et al. |
| 2001/0041227 A1 | 11/2001 | Hislop |
| 2002/0166739 A1 | 11/2002 | Naerheim |
| 2003/0109903 A1 | 6/2003 | Berrang et al. |
| 2003/0123215 A1 | 7/2003 | Allen et al. |
| 2004/0023101 A1 | 2/2004 | Jacobson et al. |
| 2004/0116976 A1 | 6/2004 | Spadgenske |
| 2004/0128016 A1 | 7/2004 | Stewart |
| 2006/0025866 A1 | 2/2006 | Serafin, Jr. et al. |
| 2006/0247714 A1 | 11/2006 | Taylor et al. |
| 2006/0259093 A1 | 11/2006 | Stevenson et al. |
| 2007/0041164 A1 | 2/2007 | Greenberg et al. |
| 2007/0183118 A1 | 8/2007 | Fu et al. |
| 2007/0217121 A1 | 9/2007 | Fu et al. |
| 2007/0276389 A1 | 11/2007 | Franke et al. |
| 2008/0060834 A1 | 3/2008 | Eck et al. |
| 2008/0071313 A1 | 3/2008 | Stevenson et al. |
| 2008/0119906 A1 | 5/2008 | Starke |
| 2008/0203917 A1 | 8/2008 | Maya |
| 2008/0269831 A1 | 10/2008 | Erickson |
| 2009/0079517 A1 | 3/2009 | Iyer |
| 2009/0192578 A1 | 7/2009 | Biggs |
| 2009/0281586 A1 | 11/2009 | Lim |
| 2009/0309459 A1 | 12/2009 | Ogashiwa et al. |

(56) References Cited

U.S. PATENT DOCUMENTS

| | | | |
|---|---|---|---|
| 2010/0022861 A1 | 1/2010 | Cinbis et al. |
| 2010/0023086 A1 | 1/2010 | Lim |
| 2010/0109966 A1 | 5/2010 | Mateychuk et al. |
| 2010/0121438 A1 | 5/2010 | Jarvik |
| 2010/0241206 A1 | 9/2010 | Truex et al. |
| 2010/0258342 A1 | 10/2010 | Parker |
| 2011/0032658 A1 | 2/2011 | Iyer |
| 2011/0034965 A1 | 2/2011 | Troetzschel et al. |
| 2011/0034966 A1 | 2/2011 | Troetzschel et al. |
| 2011/0048770 A1 | 3/2011 | Reiterer et al. |
| 2011/0094768 A1 | 4/2011 | Davis et al. |
| 2011/0106228 A1 | 5/2011 | Reiterer et al. |
| 2011/0186349 A1 | 8/2011 | Troetzschel et al. |
| 2011/0190885 A1 | 8/2011 | Troetzschel et al. |
| 2011/0232961 A1 | 9/2011 | Teske |
| 2011/0232962 A1 | 9/2011 | Teske |
| 2012/0006576 A1 | 1/2012 | Barry et al. |
| 2012/0127627 A1 | 5/2012 | Brendel et al. |
| 2012/0193117 A1 | 8/2012 | Specht et al. |
| 2012/0193118 A1 | 8/2012 | Kempf et al. |
| 2012/0193119 A1 | 8/2012 | Kempf et al. |
| 2012/0193125 A1 | 8/2012 | Pavlovic et al. |
| 2012/0193141 A1 | 8/2012 | Reisinger et al. |
| 2012/0194981 A1 | 8/2012 | Kempf et al. |
| 2012/0197326 A1 | 8/2012 | Pavlovic |
| 2012/0197327 A1 | 8/2012 | Specht |
| 2012/0197335 A1 | 8/2012 | Reisinger |
| 2012/0197368 A1 | 8/2012 | Reisinger |
| 2012/0200011 A1 | 8/2012 | Pavlovic |
| 2012/0203294 A1 | 8/2012 | Troetzschel |
| 2012/0319319 A1 | 12/2012 | Parker et al. |
| 2013/0035733 A1 | 2/2013 | Breyen et al. |
| 2013/0060312 A1* | 3/2013 | Iyer et al. .................. 607/116 |
| 2013/0070387 A1 | 3/2013 | Stevenson et al. |
| 2013/0127567 A1 | 5/2013 | Iyer et al. |
| 2013/0138186 A1* | 5/2013 | Iyer et al. .................. 607/116 |
| 2013/0138187 A1 | 5/2013 | Iyer et al. |
| 2013/0184797 A1 | 7/2013 | Tang et al. |
| 2013/0286536 A1 | 10/2013 | Iyer et al. |
| 2013/0299233 A1 | 11/2013 | Troetzschel et al. |
| 2014/0008121 A1 | 1/2014 | Troetzschel et al. |
| 2014/0144014 A1 | 5/2014 | Troetzschel et al. |
| 2014/0262494 A1 | 9/2014 | Reisinger et al. |
| 2014/0345934 A1 | 11/2014 | Markham et al. |
| 2014/0368298 A1 | 12/2014 | Reisinger |
| 2014/0371835 A1* | 12/2014 | Powell .................. B23K 1/0008 607/137 |
| 2015/0165219 A1 | 6/2015 | Markham et al. |
| 2015/0165220 A1 | 6/2015 | Markham et al. |

FOREIGN PATENT DOCUMENTS

| | | |
|---|---|---|
| DE | 102008021064 | 10/2009 |
| DE | 102009035971 | 2/2011 |
| DE | 102009035972 | 4/2011 |
| DE | 102010006837 | 8/2011 |
| DE | 102010006838 | 8/2011 |
| DE | 102010006689 | 9/2011 |
| DE | 102010006690 | 9/2011 |
| DE | 102011119125 | 5/2013 |
| EP | 0877400 | 11/1998 |
| EP | 0916364 | 5/1999 |
| EP | 1685874 | 8/2006 |
| EP | 1754511 | 2/2007 |
| EP | 2398026 | 12/2011 |
| WO | 03073450 | 9/2003 |
| WO | 2004110555 | 12/2004 |
| WO | 2008103166 | 8/2008 |
| WO | 2010091435 | 8/2010 |
| WO | 2011053540 | 5/2011 |
| WO | 2012110242 | 8/2012 |
| WO | 2012110245 | 8/2012 |
| WO | 2013075797 | 5/2013 |

OTHER PUBLICATIONS

Alloy Data, Ti-6Al-4V, Carpenter technology corp., 2000, p. 1-2.*
Exner, Horst et al., "Laser Joining of Ceramics in Liquid Phase," pp. 1-8 (Nov. 8, 2011).
Hussain, et al., "Electrical conductivity of an insulator matrix (alumina) and conductor particle (molybdenum) composites", Journal of the European Ceramic Society, vol. 23, Issue 2, Feb. 2003, pp. 315-321.
Gil et al., "Grain Growth Kinetics of Pure Titanium," Scripta Metallurgica et Materialia, vol. 33, No. 8, pp. 1361-1366 (1995).
International Search Report and the Written Opinion for International Application No. PCT/IB2014/066773 mailed Mar. 31, 2015 (12 pages).
International Search Report and the Written Opinion for International Application No. PCT/IB2014/066774 mailed May 6, 2015 (13 pages).
International Search Report and the Written Opinion for International Application No. PCT/IB2014/066775 mailed Feb. 19, 2015 (12 pages).
Restriction Requirement for U.S. Appl. No. 14/104,653 dated Jun. 26, 2015 (7 pages).
Restriction Requirement for U.S. Appl. No. 14/104,644 dated Jun. 3, 2015 (7 pages).
Office Action for U.S. Appl. No. 14/104,644 dated Jul. 31, 2015 (29 pgs).
Office Action for U.S. Appl. No. 14/104,653 dated Sep. 10, 2015 (46 pages).
Final Office Action for U.S. Appl. No. 14/104,644 dated May 5, 2016 (13 pages).
Final Office Action for U.S. Appl. No. 14/104,653 dated May 17, 2016 (21 pages).

* cited by examiner

DIRECT INTEGRATION OF FEEDTHROUGH TO IMPLANTABLE MEDICAL DEVICE HOUSING USING A GOLD ALLOY

CROSS-REFERENCE TO RELATED APPLICATIONS

This Patent Application is related to Ser. No. 14/104,644, filed on even date herewith, entitled "DIRECT INTEGRATION OF FEEDTHROUGH TO IMPLANTABLE MEDICAL DEVICE HOUSING WITH ULTRASONIC WELDING" and Ser. No. 14/104,653, filed on even date herewith, entitled "DIRECT INTEGRATION OF FEEDTHROUGH TO IMPLANTABLE MEDICAL DEVICE HOUSING BY SINTERING", all of which are incorporated herein by reference.

BACKGROUND

Implantable medical devices, such as cardiac pacemakers, cardiac defibrillators, and neurostimulators, receive and/or deliver electrical signals to/from portions of the body via sensing and/or stimulating leads. Implantable medical devices typically include a metal housing (typically titanium) having a hermetically sealed interior space which isolates the internal circuitry, connections, power sources, and other device components from body fluids. A feedthrough device (often referred to simply as a feedthrough) establishes electrical connections between the hermetically sealed interior space and the exterior bodily fluid side of the device.

Feedthroughs typically include an insulator (typically ceramic) and electrical conductors or feedthrough pins which extend through the insulator to provide electrical pathways between the exterior and the hermetically sealed interior. A frame-like metal ferrule is disposed about a perimeter surface of the insulator, with the ferrule and insulator typically being joined to one another via a brazing or soldering process. The ferrule is configured to fit into a corresponding opening in the metal housing, with the ferrule being mechanically and hermetically attached to the housing, typically via laser welding. The insulator electrically insulates the feedthrough pins from one another and from the metal ferrule/housing.

The ferrule is typically joined to insulator via a welding or brazing process. However, the high temperatures employed by such processes heats the titanium of the housing about the perimeter of the opening to levels that cause a structural change in the titanium, commonly referred to as "grain growth". This structural change can distort the dimensions of the opening and cause the titanium about the perimeter of the opening to become less rigid, each of which can result in a weaker joint between the ferrule and the housing.

Additionally, machining the ferrule (typically from pure titanium) to provide a high tolerance gap between the ferrule and the insulator (about 10-50 μm) which is necessary to achieve a quality braze joint is demanding and costly. Furthermore, if the gap is not maintained during the brazing process, or if the brazing process itself is not properly performed, a weak joint may be formed that can lead to premature failure of the implantable device.

For these and other reasons there is a need for the embodiments of the present disclosure.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
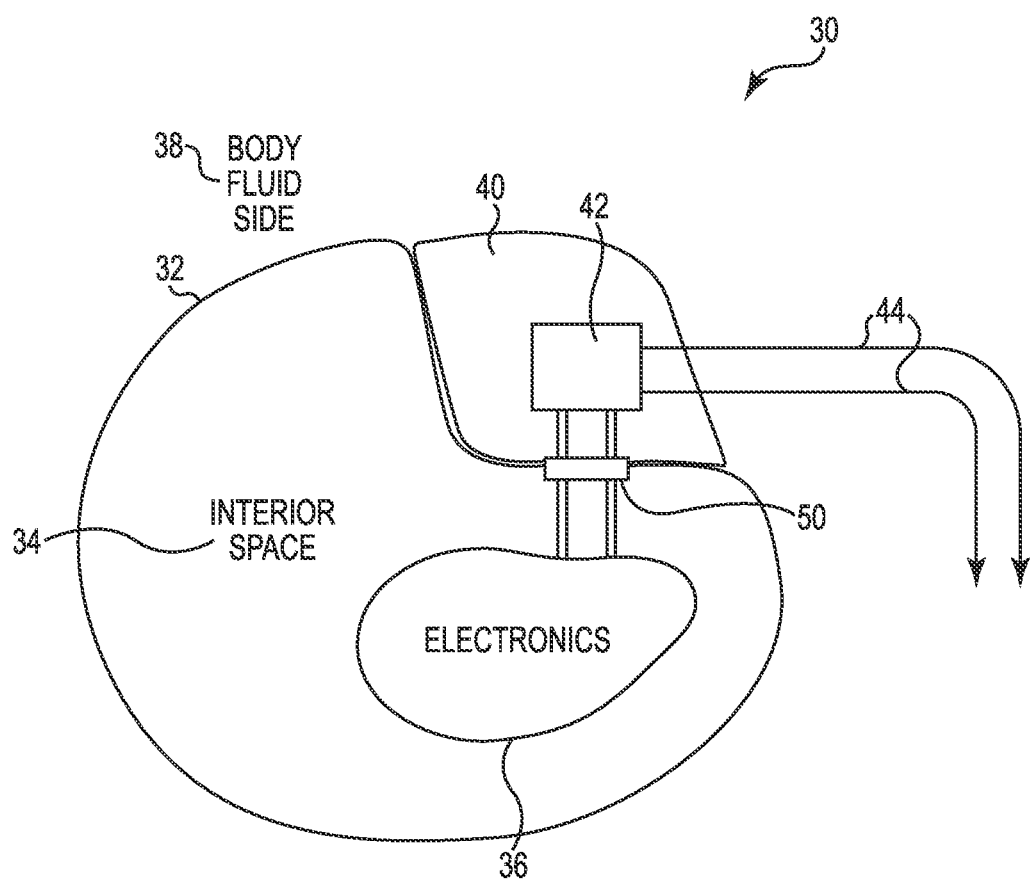
FIG. 1 generally illustrates an example of an implantable medical device according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

In accordance with one embodiment, the present disclosure provides a method of attaching a feedthrough to a titanium housing of an implantable medical device. A titanium housing is provided with a flange forming a recess about an opening through the housing, the opening disposed within the recess. The feedthrough is positioned within the recess so as to form a gap between the flange and an insulator of the feedthrough. A braze preform is positioned within the recess about the insulator, the braze preform comprising a biocompatible braze material having a melting point less than a β-transus temperature of the titanium of the housing. The braze preform is melted at a temperature less than the β-transus temperature of the titanium of the housing such that the melted braze material fills at least the gap. The braze material is cooled to form a braze joint which bonds the insulator to the housing and hermetically seals the opening. In one embodiment, a surface of the insulator to which the braze joint is bonded is metallized prior to positioning the feedthrough within the recess.

In one embodiment, the braze preform comprises a gold alloy. In one embodiment, the gold alloy consists of gold and germanium. In one embodiment, the gold alloy consists of gold and indium. In one embodiment, the gold alloy consists of gold, silver, platinum, and zinc. In one embodiment, the gold alloy consists of gold, silver, platinum, copper, and zinc.

According to one embodiment, melting the braze preform includes heating the braze preform to a temperature not exceeding 870° C. In one embodiment, melting the braze preform includes heating the braze preform to a temperature not exceeding 710° C. In one embodiment, melting the braze preform includes heating the braze preform to a temperature not exceeding 487° C. In one embodiment, melting the braze preform includes heating the braze preform to a temperature not exceeding 361° C.

Embodiments described herein for attaching the insulator of a feedthrough device directly to the device housing using a gold alloy having a low-temperature melting point provide advantages over known processes of attaching a feedthrough device to device housing. First, attaching the feedthrough directly to the housing using such a gold alloy eliminates the need for a ferrule (such as ferrule 56 of FIG. 2). By directly integrating the feedthrough to the housing using such a gold alloy, as opposed to conventional techniques which integrate the feedthrough to the housing using a ferrule, the shortcomings associated with such a ferrule (e.g. high-temperature brazed/welded joint, machining requirements, costs) are eliminated. Additionally, when combined with the use of cermet for conductive elements of the feedthrough, the present disclosure provides a feedthrough which is completely devoid of high-temperature welds/brazes.

Additionally, by employing a low-temperature brazing process using gold-alloys as described herein at temperatures below the β-transus temperature of titanium of the device housing, grain growth within the titanium material of the housing is greatly reduced relative to conventional techniques which employ high-temperature brazing or welding processes to attach feedthrough devices to housings via a ferrule, particularly in the region of the housing about a perimeter of an opening in which the feedthrough is disposed. Reducing the grain growth of the titanium of housing reduces dimensional distortions of housing as compared to conventional techniques, at least to levels within design tolerances, thereby providing stronger and more consistent hermetic seals between the insulator and the housing.

One aspect of the present disclosure provides an implantable medical device including a titanium housing with a flange defining a recess about an opening through the housing, the opening disposed within the recess. A feedthrough is disposed within the recess with a gap between an insulator of the feedthrough and the flange. A braze joint is disposed between the insulator and the flange that fills at the gap and hermetically seals the insulator to the housing, the braze joint comprising a biocompatible gold alloy having a melting point less than the β-transus temperature of the titanium of the housing. In one embodiment, a surface of the insulator to which the braze joint is bonded includes a metalized layer.

According to one embodiment, the biocompatible gold alloy consists of gold and germanium. In one embodiment, the gold alloy consists of gold and indium. In one embodiment, the gold alloy consists of gold, silver, platinum, and zinc. In one embodiment, the gold alloy consists of gold, silver, platinum, copper, and zinc.

According to one embodiment, the melting point of the gold alloy does not exceed 870° C. In one embodiment, the melting point of the gold alloy does not exceed 710° C. In one embodiment, the melting point of the gold alloy does not exceed 487° C. In one embodiment, the melting point of the gold alloy does not exceed 361° C.

According to one embodiment, the titanium of the housing within 0.25 inches of the opening has a grain size not exceeding 150 μm. In one embodiment, the titanium of the housing within 0.25 inches of the opening has a grain size not exceeding 100 μm.

A further embodiment of the present disclosure provides a method of attaching a feedthrough to a titanium housing of an implantable medical device, the method comprising. The method includes providing the housing with a flange defining a recess about an opening through the housing. A feedthrough is positioned within the recess so as to form a gap between the flange and an insulator of the feedthrough. A braze material comprising a biocompatible gold alloy having a melting temperature less than a β-transus temperature of the titanium of the housing is melted to fill at least the gap and form a braze joint which bonds the insulator to the housing and hermetically seals the opening, including melting the braze material at a temperature less than the β-transus temperature of the titanium of the housing and for a duration that limits grain growth of the titanium of the housing within 0.25 inches of the opening to a grain size not exceeding 150 um.

FIG. 1 is a block and schematic diagram generally illustrating one embodiment of an implantable medical device 30, such as a cardiac pacemaker for example. Implantable medical device 30 includes a hermetically sealed metal case our housing 32, typically formed of titanium, which defines a hermetically sealed interior space 34 in which device electronics 36 are disposed and protected from fluids of the body fluid side 38 external to housing 32. A header 40 attaches to housing 32 and includes a connector block 42 which typically includes one or more sockets for connecting to one or more sensing and/or stimulating leads 44 that extend between implantable medical device 30 and desired regions of the body, such as the human heart and brain, for example. A feedthrough device 50 establishes electrical pathways or connections through housing 32 that maintain the integrity of hermetically sealed interior space 34 and provide electrical connection of leads 44 to internal device electronics 36.

Figure 2:
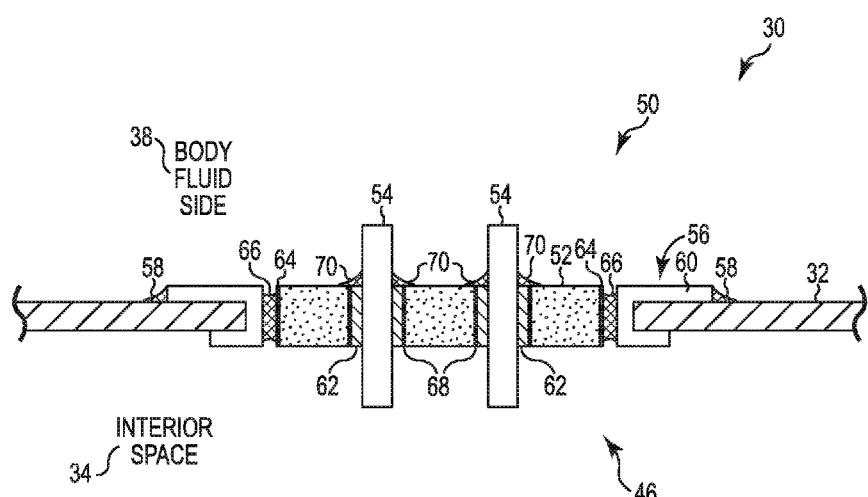
FIG. 2 illustrates a feedthrough device in an implantable in accordance with the prior art.

FIG. 2 is a cross-sectional view illustrating portions of an implantable medical device, such as medical device 30 of FIG. 1, including metal housing 32 having an opening 46 in which a conventional feedthrough device 50 is positioned. Feedthrough device 50 includes an insulator 52 and feedthrough pins or conducting elements 54. A ferrule 56, comprising a frame-like metal structure, holds insulator 52 and is configured to fit into opening 46 for attachment to housing 32. Ferrule 56 is a bio-compatible material, typically titanium, which is mechanically and hermetically attached to housing 32 by laser welds 58, or similar techniques. Ferrule 56, as illustrated in FIG. 2, sometimes includes a flange 60 to further aid in securing ferrule 56 to housing 32.

Conducting elements 54 extend through openings or vias 62 in insulator 52 and are formed of an electrically conductive material so as to provide electrically conductive pathways from the external body fluid side 38 of housing 32 to hermetically sealed interior space 34. Insulator 52 is formed of a non-electrically conductive material, such as a ceramic material, aluminum oxide ($Al_2O_3$) for example, and electrically isolates conducting elements 54 from one another and from ferrule 56 and housing 32.

When attaching insulator 52 and ferrule 56 to one another, a perimeter surface of insulator 52 is typically metalized (through a sputter coating process, for example) to provide a thin metal coating 64 thereon. Ferrule 56 is then joined to insulator 52 via metal coating 64 using a braze 66, such as of gold, for example, to form a biocompatible and hermetic seal. Similarly, interior surface of vias 62 are provided with a metal coating 68 and a braze 70 (e.g. gold) is used to couple conducting elements 54 to insulator 52 and form a biocompatible and hermetic seal.

In order to achieve a quality braze, and thereby a quality hermetic seal, a proper gap must be maintained between ferrule 56 and insulator 52 during the brazing process (typically about 10-50 um) so that the brazing material (e.g. gold) is properly drawn into the gap by capillary action to create a strong and reliable braze 66. Forming ferrule 56, typically via machining processes, to meet the tight tolerances required to provide the proper gap with insulator 52 as well as to the dimensions of opening 46 in housing 42 is time consuming and costly. Also, during the brazing process, intermetallics are formed between the brazing material (e.g. gold) and the material (e.g. titanium) of ferrule 56, with the intermetallics being brittle as compared to the brazing material. If the gap between ferrule 56 and insulator 52 is too small, the amount of intermetallics may be large relative to the amount of pure brazing material (e.g. gold) resulting in a brittle braze 66 that may crack and comprise the hermitic seal.

Additionally, heat from the brazing (or welding) of ferrule 56 to housing 32 can cause structural changes in the titanium of housing 32 about opening 46 (and to ferrule 56) due to "grain growth" in the titanium. Such "grain growth" can cause undesirable dimensional changes in opening 46 and can cause the titanium about the perimeter of opening 46 to become less rigid (i.e. more flexible), which such changes leading to a weakened or defective joint.

All polycrystalline materials, including titanium, are made of closely packed atoms, with "regions of regularity" within these closely packed atoms (i.e. where the atoms have a regular structure, such as 8-co-ordination and 12-co-ordination, for example) being referred to as "crystal grains". Metal consists of a vast number of these crystal grains. The boundaries of these crystals (i.e. "grain boundaries") are locations at which atoms have become misaligned (i.e. the regular structure is discontinuous). Metals having smaller grains and, thus, more grain boundaries, are harder than metals having larger grains, which have fewer grain boundaries and, as a result, are softer and more flexible.

Heating of a metal, such as titanium, causes the atoms to move into a more regular arrangement, thereby decreasing the overall number of crystal grains but increasing the grain size of the remaining grains (i.e. the number of grains per unit volume decreases). The process by which the average grain size increases, so-called "grain growth", rearranges the crystalline structure of the metal and can cause dimensional changes (i.e. dimensional deformation) of the metal and cause the metal to become more flexible.

Titanium has an α-phase, which has a close-packed hexagonal crystal structure, and a β-phase, which has centered-cubic crystal structure and that is more open and prone to grain growth than the hexagonal structure. Titanium transitions from α-phase to β-phase, the so-called β-transus, when heated to or above a certain temperature, referred to as the β-transus temperature. The β-transus temperature is affected by impurities in the titanium (e.g. iron, carbon, hydrogen), but typically occurs at about 880° C. in commercially-pure titanium. Commercially pure titanium, as opposed to titanium alloys having additive such as aluminum (Al), typically has a microstructure of primarily α-phase grains having an average grain size in the range of 10-40 µm.

The grain growth of a metal, including titanium, is a function of the time and temperature for which a metal is heated. For example, while the average grain size of commercially-pure titanium increases when heated to temperatures below the β-transus temperature, such grain growth accelerates rapidly when the titanium is heated to a temperature at or above the β-transus temperature and the titanium transitions from α-phase to β-phase. For instance, the average grain size of commercially-pure titanium has been shown to increase in from about 10-40 µm to about 70 µm when heated at 700° C. for 120 minutes, to about 100 µm when heated at 750° C. for 120 minutes, and to about 180 µm when heated at 800° C. for 120 minutes. However, the average grain size of commercially-pure titanium has been shown to increase in from about 10-40 µm to about 350 µm when heated at 1000° C. for 120 minutes, and to about 425 µm when heated at 1100° C. for 120 minutes.

With reference to conventional feedthrough 50 of FIG. 2, attaching ferrule 56 to housing 32 by laser welding or brazing (e.g. gold braze) heats housing 32 to a temperature well above the β-transus temperature of titanium, resulting in rapid grain growth in the titanium of housing 32. For example, the average grain size may increase by 300 µm or more. Such grain growth causes dimensional distortions in housing 32 that can cause opening 46 to be outside of specified tolerances and causes the titanium about the perimeter of opening 46 to become less rigid, each of which can result in a poor or defective seal being formed between housing 32 and feedthrough 50.

Figure 3:
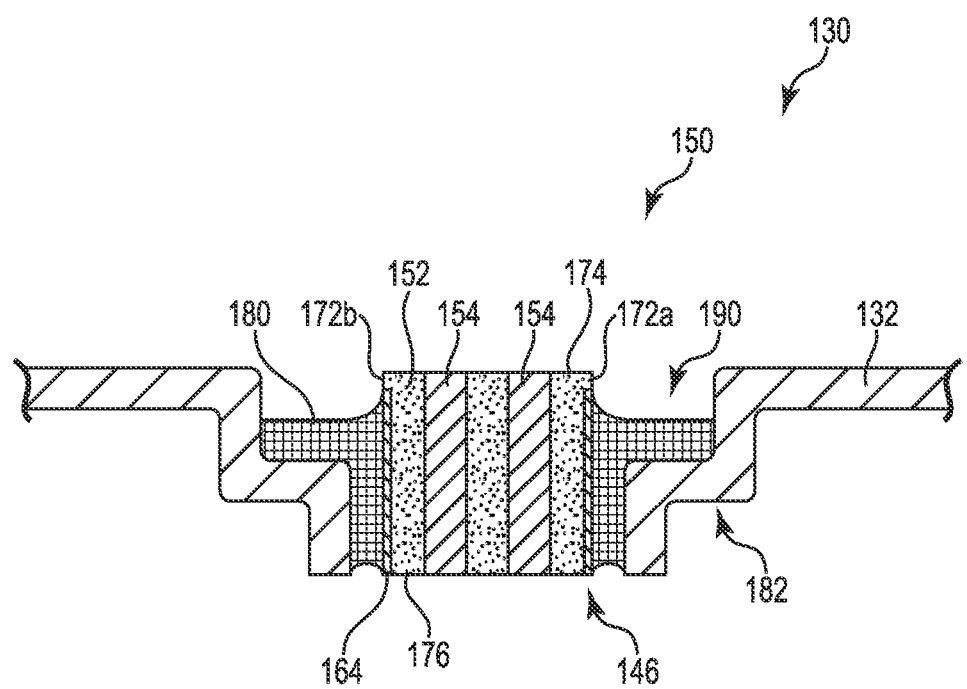
FIG. 3 illustrates a cross-sectional view of a feedthrough in an implantable medical device in accordance with one embodiment.

FIG. 3 is a schematic diagram illustrating portions of an implantable medical device 130 including a feedthrough 150 according to one embodiment of the present disclosure. Feedthrough 150 includes an insulator 152 and conducting elements 154 extending therethrough. As will be described in greater detail below, feedthrough 150 is attached directly to housing 132 via insulator 152 with a braze joint 180 that is formed at low-temperatures, at least at temperatures below the β-transus temperature of the titanium of housing 132. According to one embodiment, as will be described in greater detail below, braze joint 180 is formed of a gold alloy having a melting point less than the β-transus temperature of the titanium of housing 132.

According to the embodiment of FIG. 3, housing 12 includes a flange 182 forming a stepped recess 190 about opening 146. Feedthrough 150 is disposed within recess 190 over opening 146, with recess 190 serving to retain the gold alloy material of braze joint 180 and surfaces of flange 182 providing surfaces to which braze joint 180 is able to bond. According to the embodiment of FIG. 3, and based on the geometry flange 182, portions of side surfaces 172*a*, 172*b* of insulator 152 to which braze joint 180 is configured to bond are provided with a metalized layer 164. According to one embodiment, metalized layer 164 comprises a sputter coated or electroplated layer of a biocompatible metal such niobium, platinum, palladium, titanium, and gold, for example.

Upper and lower surfaces 174 and 176 of insulator 152 do not contact braze joint 180 and are not provided with a metallized surface.

By attaching feedthrough 150 directly to housing 132 via insulator 152, such as illustrated by the embodiment of FIG. 3, the need for a ferrule (such as ferrule 56 of FIG. 2) is eliminated, thereby eliminating the costs of manufacturing such a ferrule. Additionally, by attaching feedthrough 150 to housing 132 using brazing techniques at reduced temperatures relative to conventional welding or brazing techniques, dimensional distortions of housing 132 due to the high temperatures and grain growth of titanium are substantially reduced (i.e. at least to levels that maintain dimensions of housing 32 within specified tolerances) and the titanium about the perimeter of opening 146 remains in a more rigid state.

While FIG. 3 a cross-sectional view illustrating portions housing 132, particularly the location where feedthrough 150 attaches to housing 132 to seal opening 146, implantable medical device 130 may include additional features similar to those described with respect to medical device 30 of FIG. 1. According to one embodiment, housing 132 is formed of titanium and defines a sealed interior space 134 in which device electronics are disposed and protected from fluids of body fluid side 138 external to housing 132. According to one embodiment, a header, similar to header 40 of FIG. 1, for example, maybe also provided which attaches to housing 132 and includes a connector block that includes a connector block having one or more sockets for connecting to one or more sensing and/or stimulating leads.

Similar to that described above with regard to FIG. 3, feedthrough 150 establishes electrical connections or pathways from body fluid side 138 to the interior space 134 of housing 132 while maintaining the integrity of hermetically sealed interior space 134 via conducting elements 154 which pass through insulator 152. According to one embodiment, insulator 152 is a glass or ceramic material, such as aluminum oxide ($Al_2O_3$). According to on embodiment, conducting elements 154 are formed of a cermet.

In the context of one embodiment, the terms, "cermet" or "cermet-containing," refers composite materials made of ceramic materials in a metallic matrix (binding agent). These are characterized by their particularly high hardness and wear resistance. The "cermets" and/or "cermet-containing" substances are cutting materials that are related to hard metals, but contain no tungsten carbide hard metal and are produced by powder metallurgical means. A sintering process for cermets and/or cermet-containing elements proceeds is the same as that for homogeneous powders, except that the metal is compacted more strongly at the same pressuring force as compared to the ceramic material. The cermet-containing bearing element has a higher thermal shock and oxidation resistance than sintered hard metals. In most cases, the ceramic components of the cermet are aluminum oxide ($Al_2O_3$) and zirconium dioxide ($ZrO_2$), whereas niobium, molybdenum, titanium, cobalt, zirconium, chromium and platinum are conceivable as metallic components.

According to one embodiment, such as illustrated by FIG. 3, the ceramic (e.g. $Al_2O_3$) of insulator 152 and the cermet of conducting elements 154 are formed in a first process such that an interface between insulator 152 and conducting elements 154 are hermetically sealed without the use of a braze or solder. According to one example of such an embodiment, the ceramic of insulator 152 is a multi-layer ceramic sheet into which a plurality of vias is introduced. The cermet of conducting elements 154 is then introduced into the vias. In one embodiment, both materials are introduced in a green state, and the combination is fired together.

According to such an embodiment, the joining of insulator 152 with conducting elements 154 forms a hermetic seal without the use of braze or solder. By combining the brazing of insulator 152 to housing 132 in the absence of ferrule with the cermet conducting elements 154 as described above, feedthrough 150, according to one embodiment, is formed entirely without the use of a braze or solder joint.

Figure 4:
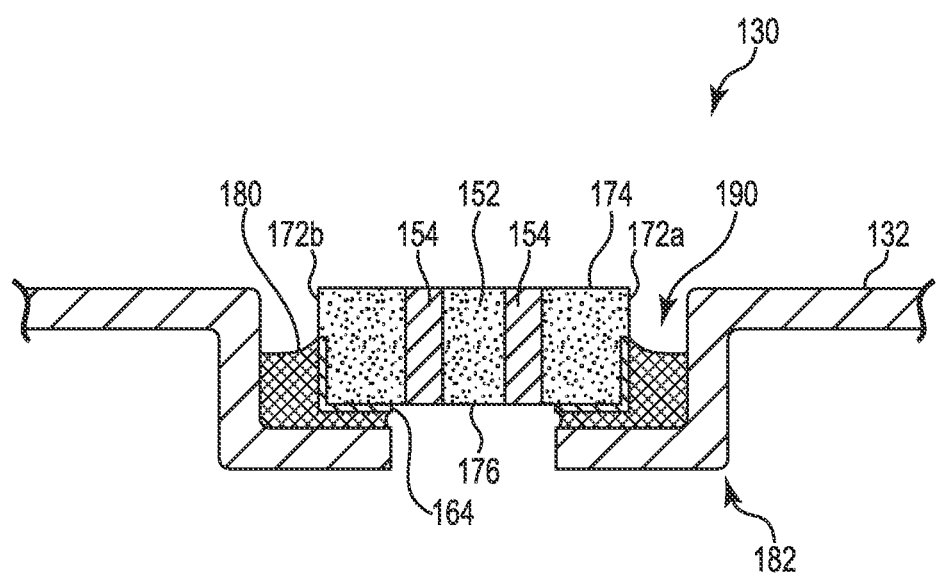
FIG. 4 is cross-sectional view illustrating a feedthrough in an implantable medical device including according to one embodiment.

FIG. 4 is schematic diagram illustrating implantable medical device 130 according to one embodiment of the present disclosure. The embodiment of FIG. 4 is similar to that of FIG. 3, except that the geometry of flange 182 does not form a recess 190 which is stepped in shape, and that feedthrough 150 is positioned within recess 190 over opening 146 and overlaps with flange 182. With feedthrough 152 overlapping flange 182, braze joint 180 contacts portions of side surfaces 172a, 172b and lower surface 176 of braze joint 190, with such portions being provide with metalized layer 164.

In the embodiments of FIGS. 3 and 4, flange 182 defines recess 190 in which feedthrough 150 is disposed and defines surfaces to which braze joint 180 bonds. It is noted that FIGS. 3 and 4 illustrate only two embodiments of any number of geometries which may be employed by flange 182 to form recess 190.

Figure 5:
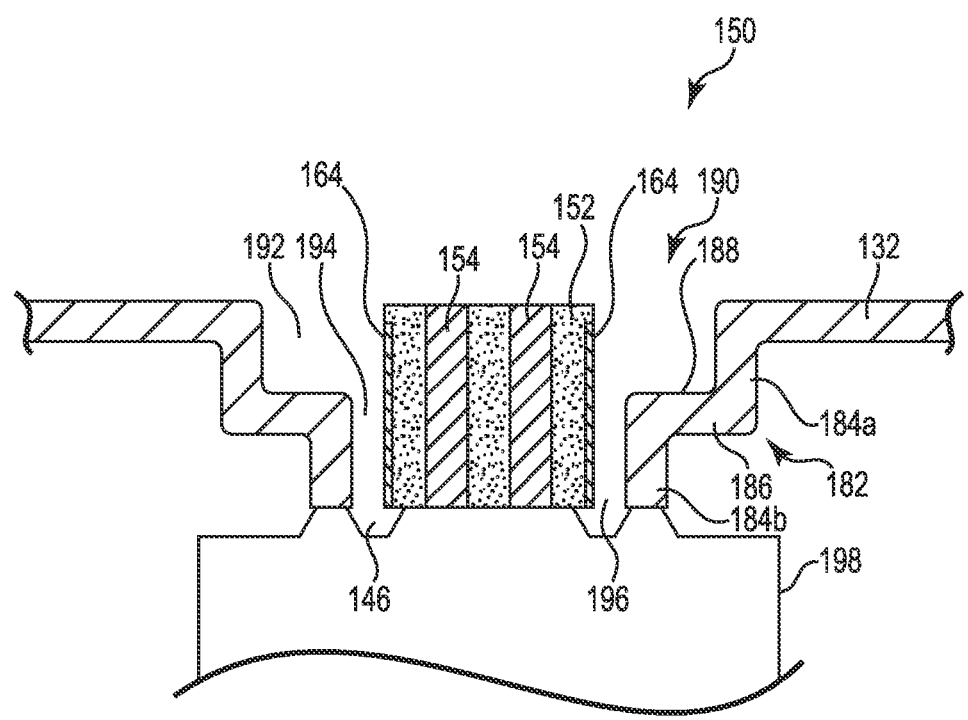
FIG. 5 is a block and schematic diagram illustrating a method of attaching a feedthrough to a housing using a brazing process according to one embodiment.
Figure 6:
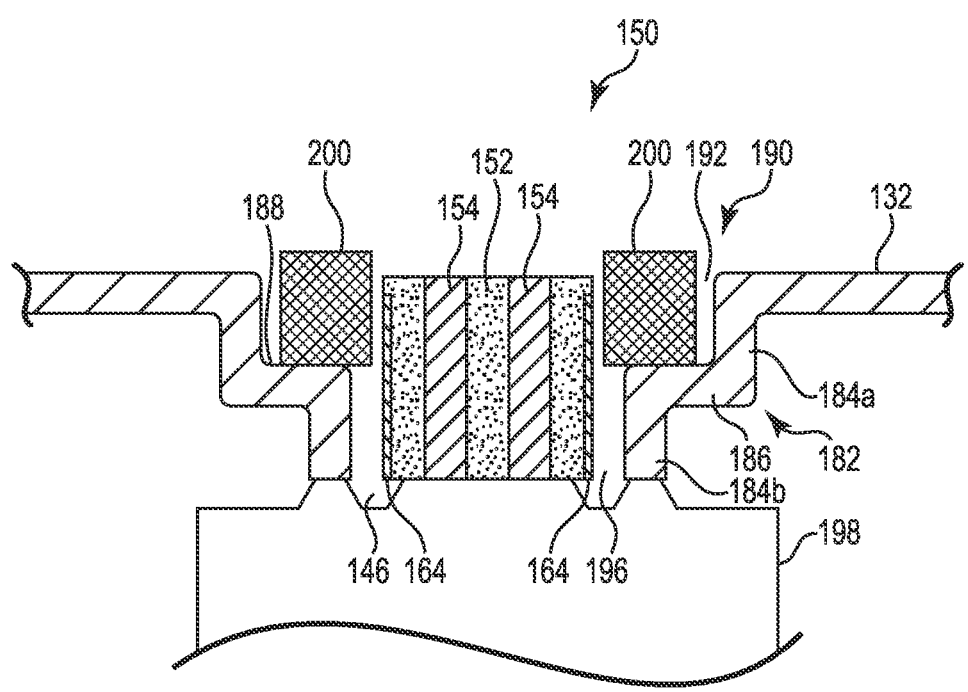
FIG. 6 is a block and schematic diagram illustrating a method of attaching a feedthrough to a housing using a brazing process according to one embodiment.
Figure 7:
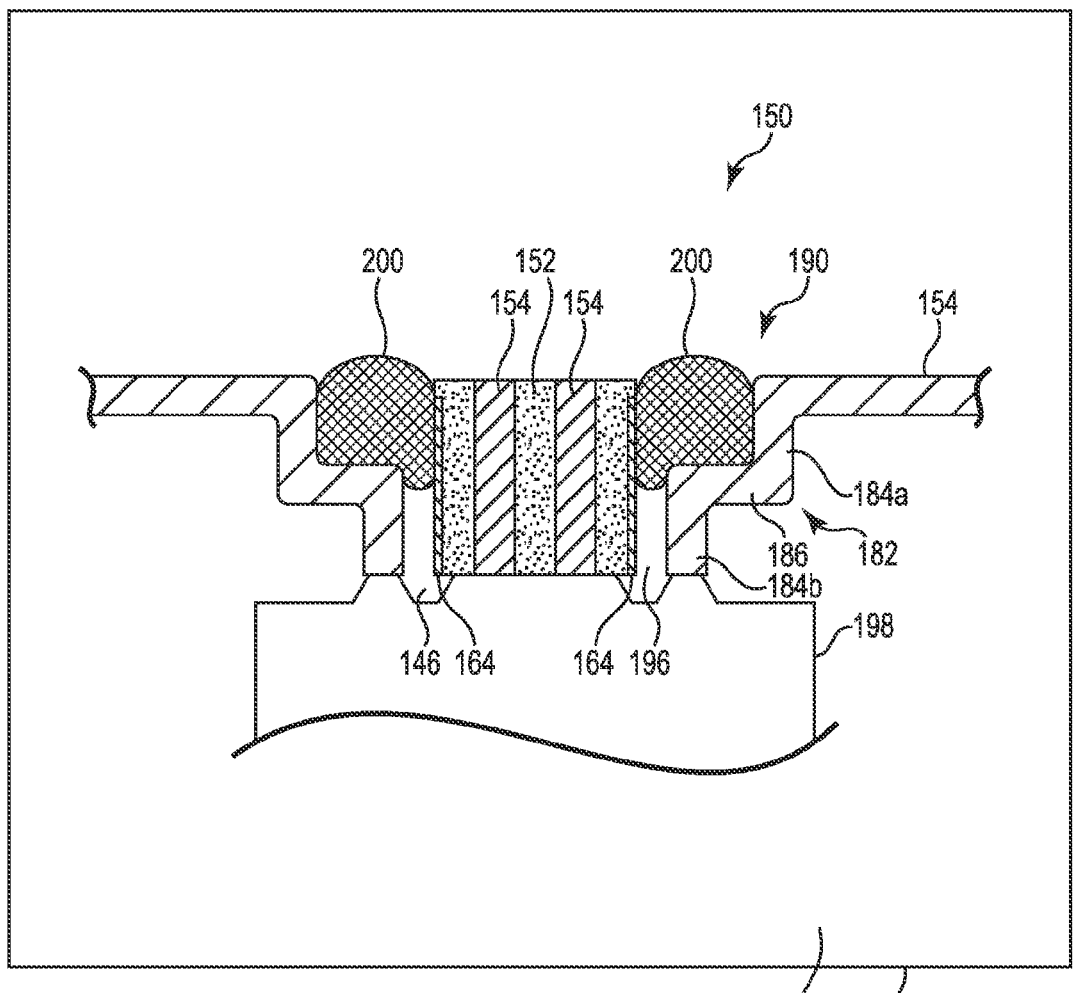
FIG. 7 is a feedthrough to a housing using a brazing process according to one embodiment.

FIGS. 5 through 7 below illustrate and describe embodiments for attachment of feedthrough 150 to housing 132 using low-temperature brazing according to the present disclosure. With reference to FIG. 6, housing 132 of an implantable medical device is provided, such as implantable medical device 130 of FIG. 3. Housing 132 includes integral flange 182 having a pair of vertical portions 184a, 184b and a horizontal portion 186 forming recess 190 with a stepped configuration, with a surface of horizontal portion 186 forming a seating surface 188 within recess 190.

Recess 190 includes an upper portion 192 and a lower portion 194, the upper portion 192 having a lateral dimension greater than that of lower portion 194. According to one embodiment, feedthrough 150 and recess 190 are both circular in shape such that the lateral dimension comprises an inner diameter, with upper portion 192 having a larger inner diameter than that of lower portion 194.

As illustrated, according to one embodiment, a support element 198 is provided to support housing 132 and feedthrough 150. Feedthrough 150 is positioned so as to be centered within recess 190 over opening 146 and form a gap 196 between insulator 152 and vertical portion 184b of flange 182. The flange 182 is formed so that gap 196 has a dimension necessary to enable braze material of braze joint 180 to be drawn into and flow within gap 196 by capillary action. According to one embodiment, gap 196 has a distance in the range of 10-50 μm.

With reference to FIG. 6, after positioning feedthrough 150 within recess 190, a preform 200 of biocompatible brazing material is disposed within upper portion 192 of recess 190 and is seated on seating surface 188 so as to be positioned about a circumference of feedthrough 150. According to one embodiment, as described above, the brazing material of preform 200 has a melting point or liquidous temperature less than a β-transus temperature of the titanium of housing 132. According to one embodiment, as described above, the brazing material of preform 200 is a gold alloy having a melting point or liquidous temperature not greater than 870° C. According to one embodiment, the gold alloy of preform 200 has a melting point not greater than 850° C. According to one embodiment, the gold alloy of preform 200 has a melting point not greater than 710° C. According to one embodiment, the gold alloy of preform 200 has a melting point not greater than 487° C. According to one embodiment, the gold alloy of preform 200 has a melting point not greater than 361° C.

According to one embodiment, preform 200 comprises one of Au—Ga (Gold-Gallium), Au—Ge (Gold-Germanium), and Au—In (Gold-Indium). According to one embodiment, preform 200 is a gold alloy comprising 73% gold, 12% silver, 0.45% platinum, and 14.5% zinc and having a melting point of 710° C. According to one embodiment, preform 200 is a gold alloy comprising 76% gold, 9% silver, 3.90% platinum, 6.10% copper, and 4.5% zinc and having a melting point of 870° C. According to one embodiment, preform 200 is a gold alloy comprising 88% gold and 12% germanium and having a melting point of 361° C. According to one embodiment, preform 200 is a gold alloy comprising 81% gold and 19% indium and having a melting point of 487° C.

Although specific examples of gold-alloys are listed above for use as preform 200, it is noted that such list is not exhaustive and that other suitable gold alloys having low-temperature melting points, at least below the β-transus temperature of titanium, may be used for the formation of preform 200 and braze joint 180.

Referring to FIG. 7, after positioning preform 200 within upper portion 192 of recess 190, housing 132, feedthrough 150, and preform 200, along with support element 198 are placed within an oven 210 to carry out a brazing process to form finished braze joint 180 from preform 200. According to one embodiment, interior environment 212 is controlled so as to prevent the titanium materials from oxidizing and weakening a bond between housing 132, metalized layer 164, and final braze joint 180. According to one embodiment, interior 212 comprises a vacuum. According to one embodiment, interior 212 comprises an inert gas, such as argon, for example.

With reference to FIG. 7, as interior 212 of oven 210 is heated in accordance with a desired low-temperature heating profile (i.e. maximum temperature(s) less than the β-transus temperature of titanium), preform 200 begins to melt and flow into gap 196. It is noted that preform 200 is provided with a volume of brazing material required to fill gap 196 about feedthrough 150 in lower portion 194 and to fill upper portion 192 of recess 190 to a desired level.

Figure 8:
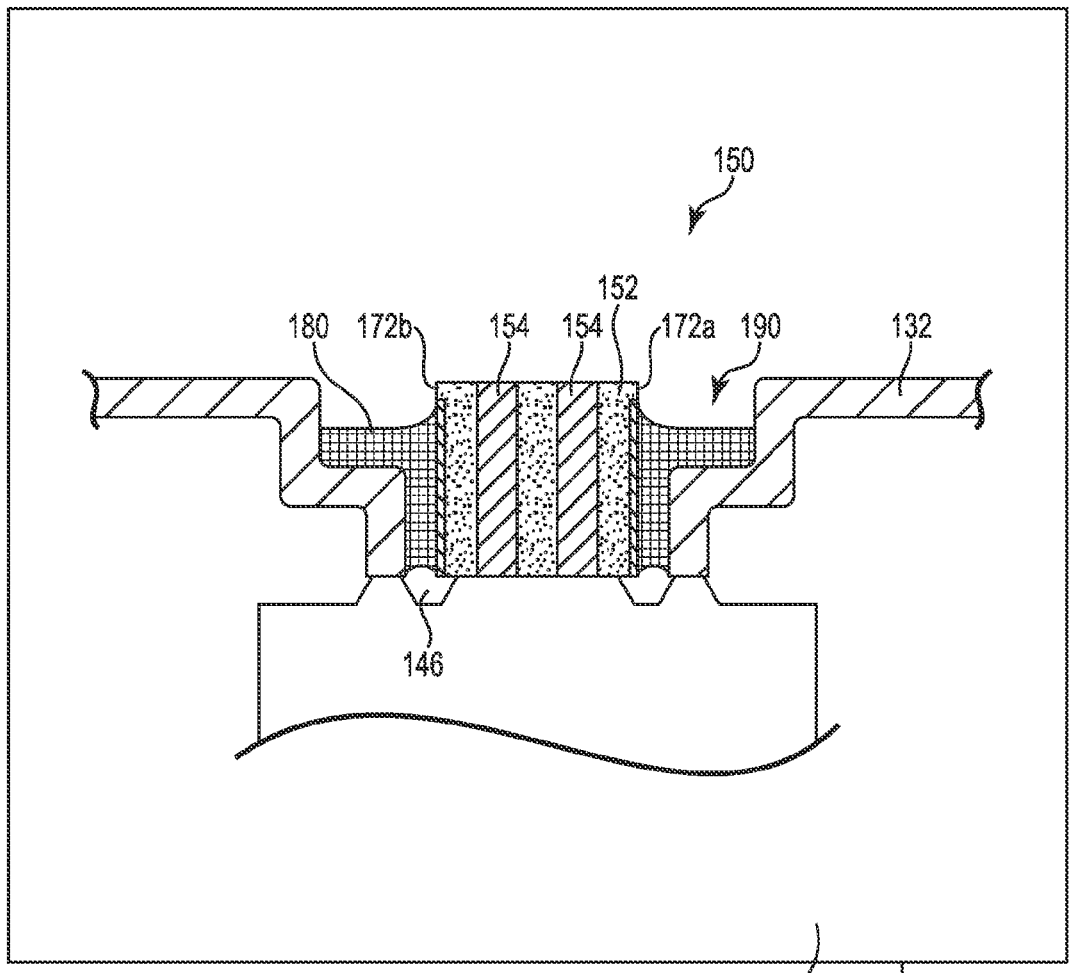
FIG. 8 is a feedthrough to a housing using a brazing process according to one embodiment.

Referring to FIG. 8, upon completion of the desired heating profile, preform 200 is completely melted and flows to fill gap 196 about feedthrough 150 in lower portion 192 of recess 190 and to fill upper portion 192 of recess 190 to a desired level. The components are then cooled so as to form finished braze joint 180 which bonds to the titanium of housing 132 and to the titanium of metalized layer 164 of insulator 152 and thereby attaches feedthrough 150 to housing 132 within opening 146. According to the embodiment of FIG. 8, after formation of finished braze joint 180, the components are removed from oven 210 to arrive at the device illustrated by FIG. 3.

Any number of scenarios are envisioned with regard to the heating of oven 210 in order to achieve an optimal braze joint 180 between housing 132 and feedthrough 150, wherein heating parameters, such as temperature and duration, may vary depending on a variety of factors, such as the type of alloy of preform 200, on a volume of alloy material employed, and on a type of geometry employed about opening 146 (e.g. a shape of recess 190), for example.

For example, according to one embodiment, where preform comprises the gold-germanium alloy described above (i.e. 88% gold, 12% germanium), a brazing profile having multiple stages is employed. During a first stage, the temperature is ramped up at a rate of 95° F./hr. until the temperature reaches 650° F. During a second stage, the temperature is held at 650° F. for 5 minutes. During a third stage, the temperature is ramped up at a rate of 40° F./hr. from 650° F. to 665° F. During a fourth stage, the temperature is held at 665° F. for 20 minutes. During a fifth stage, the temperature is ramped up at a rate of 150° F./hr. from 665° F. to 745° F. During a sixth stage, the temperature is held at 745° F. for 20 minutes. During a seventh stage, oven 210 is powered off and allowed to cool. Finally, during an eighth stage, when oven 210 cools to 600° F., a quick cool is performed to bring the oven to room temperature. Again, it is noted that any number of brazing or heating profiles may be employed, and that the above described profile is only an example of one such profile.

Figure 9:
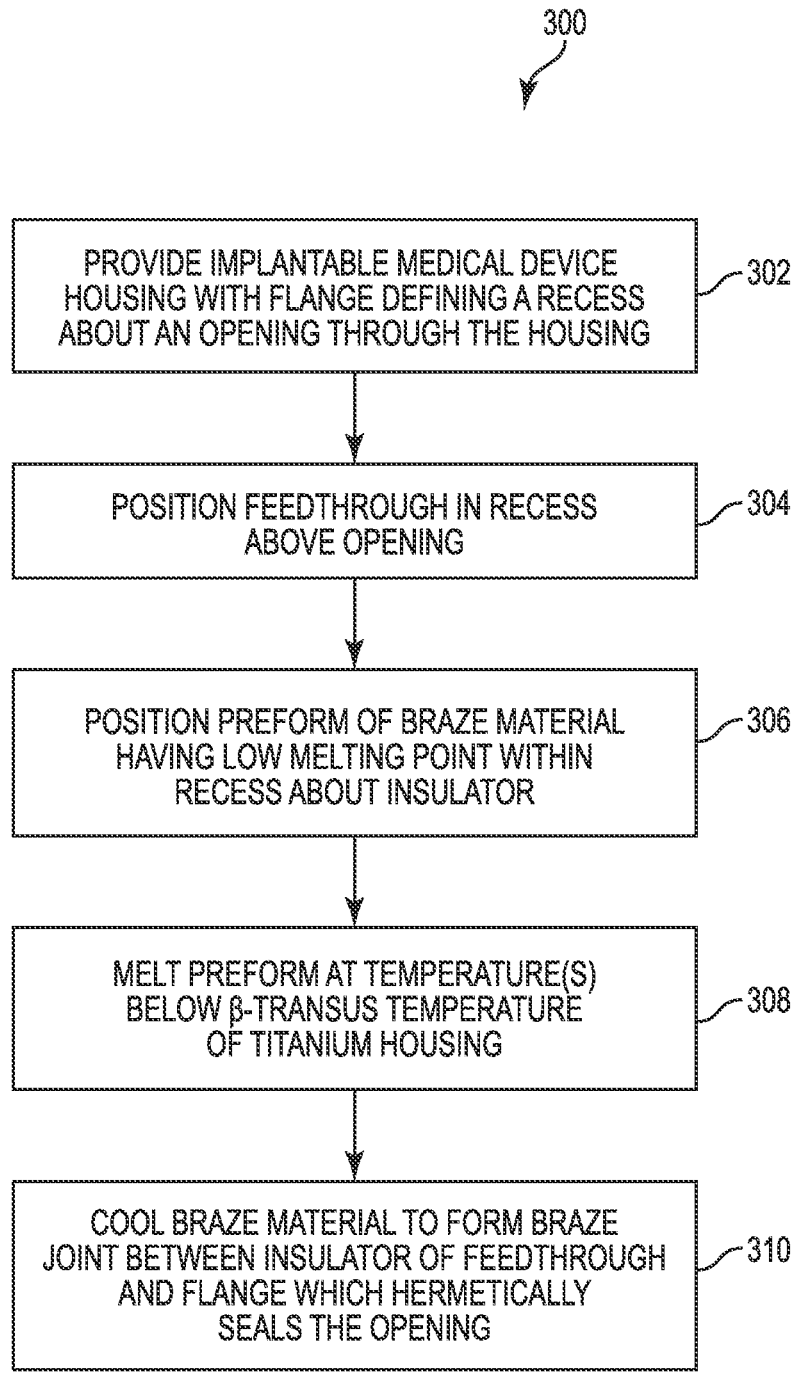
FIG. 9 is a flow diagram illustrating a method of attaching a feedthrough to a housing using low-temperature brazing according to one embodiment.

FIG. 9 is a flow diagram illustrating a process 300 for hermetically attaching a feedthrough to a housing of an implantable medical device using a low-temperature brazing process according to one embodiment of the present disclosure. Process 300 begins at 302 where a titanium housing for an implantable medical device is provided, such as housing 132 of implantable medical device 130 of FIG. 3. Housing 132 includes a flange 182 which forms a recess in housing 132 about opening 146 through housing 132, such as recess 190 of FIG. 4, with opening 146 being disposed within the recess. Flange 132 is configured to provide a seating surface within the recess, such as seating surface 188 with recess 190 as illustrated by FIG. 5.

At 304, the feedthrough is positioned within the recess over the opening so as to form a gap between an insulator of the feedthrough and the flange, such as feedthrough 150 being positioned within recess 190 so as to form a gap 192 between insulator 152 and flange 182 as illustrated by FIG. 6. According to one embodiment, housing 132 and feedthrough 150 are positioned on a support element, such as support element 198 illustrated by FIG. 6.

At 306, a preform of a braze material having a melting point below that of the β-transus temperature of the titanium of the housing is positioned on the seating surface defined by the flange about the feedthrough, such as preform 200 being positioned on seating surface 188 defined by flange 182 within recess 190 as illustrated by FIG. 6. According to one embodiment, the braze material of the preform is a gold alloy having a melting point not greater than 870° C. According to one embodiment, the braze material of the preform is a gold alloy having a melting point not greater than 361° C.

At 308, the housing, feedthrough, and braze preform are positioned within an oven, such as housing 132, feedthrough 150, and preform 200 being positioned within oven 210 having a controlled interior environment 212 as illustrated by FIG. 7. According to one embodiment, interior environment 212 of oven 210 comprises a vacuum. In one embodiment, interior environment 212 comprises and inert gas, such as argon, for example. After being placed in the oven, a brazing process is initiated to heat the interior environment 212 according to a desired brazing or heating profile, at which point braze preform 200 begins to melt and begins to be drawn into gap 196 via capillary action and to fill the upper portion 192 of recess 190, such as illustrated by FIG. 7.

According to one embodiment, the heating profile includes multiple stages whereby the heat is increased in steps, for example, such as described above with respect to FIG. 8. Regardless of a particular heating profile that is employed, according to the present disclosure, a maximum temperature of the heating profile does not exceed the β-transus temperature of the titanium of the housing 132. As the heating profile is carried out, the braze preform 200 completely melts and flows to fill gap 196 and a portion of the upper portion 192 of recess 190 as illustrated by FIG. 8.

At 310, after the braze preform 200 has completely melted such that the braze material has filled gap 196 and at least an upper portion 192 of recess 190, the housing 132, feedthrough 150, and the melted material of braze preform 200 are cooled so that the melted material of braze preform 200 hardens and forms finished braze joint 180 which bonds insulator 152 to the flange 182 of housing 132 and hermetically seals opening 146, such as illustrated by the portions of medical device 130 illustrated by FIG. 3. According to one embodiment, housing 132, feedthrough 150, and the melted material of braze preform 200 are slow-cooled to a first temperature and then quick-cooled to room temperature.

In view of the above, according to the techniques and embodiments of the present disclosure, the attachment of feedthrough 150 to housing 132 using braze joint 180 eliminates the need for a ferrule (such as ferrule 56 of FIG. 2). By directly integrating feedthrough 150 to housing 132 via braze joint 180, as opposed to conventional techniques which integrate the feedthrough to the housing using a ferrule, the shortcomings associated with such a ferrule (e.g. brazed/welded joint, machining requirements, costs) are eliminated. When combined with the use of cermet for conductive elements 154, feedthrough 150 of the present disclosure provides a feedthrough 150 for implantable medical device 130 which is completely devoid of welds and/or brazing.

Also, by using a brazing process as described herein to attach feedthrough 150 to the titanium of housing 132 at temperatures below the β-transus temperature of titanium, grain growth within the titanium material of housing 132, particularly about a perimeter of opening 146, is greatly reduced relative to conventional techniques which employ high-temperature brazing or welding processes to attach feedthrough devices to housings via a ferrule.

As described above, an average grain size of commercially pure titanium employed by housing 132, prior to brazing, is initially in the range of about 10-40 μm. According to one embodiment, attaching feedthrough 150 to housing 132 with low-temperature braze joint 180 formed in accordance with the present disclosure results in an average grain size of the titanium of housing 132 proximate to opening 132 that does not exceed 150 μm (such as when using gold alloys having melting points 750° C. or greater). According to one embodiment, attaching feedthrough 150 to housing 132 with low-temperature braze joint 180 formed in accordance with the present disclosure results in an average grain size of the titanium of housing 132 proximate to opening 132 that does not exceed 100 μm (such as when using gold alloys having melting points less than 750° C.).

As such, according to one embodiment, implantable medical device 130 according to the present disclosure, such as that illustrated by FIGS. 3 and 4, for example, is characterized by a titanium housing 132 with the distinctive structural characteristic imparted by the brazing process described herein of having an average grain size not exceeding 150 μm, at least in a region of the housing directly proximate to opening 146 (such as within 0.25" of opening 146, for example). According to one embodiment, the average grain size does not exceed 100 μm. Such a characteristic is distinctive as compared to joints formed by conventional techniques, such as welding and brazing, which result in average grain sizes greatly exceeding 150 μm, such as 300 μm or greater, for example.

By reducing the grain growth of the titanium of housing 132, dimensional distortions of housing 132 are also reduced as compared to conventional techniques, at least to levels whereby dimensions of opening 132 remain within design tolerances after attachment of feedthrough 150. According to one embodiment, dimensional changes of housing 132 do not exceed 5% relative to initial dimensions. As an example, if opening 146 is a rectangular opening having initial dimensions of 0.020"×0.040" prior to attachment of feedthrough 150, the dimensions after attachment using the brazing processes described herein will be within a range 0.019-0.021"×0.038-0.042". The reduced grain growth also results in the titanium of housing 132, particularly in the region immediately about the perimeter of housing 132, becoming less flexible and remaining more rigid as compared to conventional attachment techniques. Reducing dimensional distortions and retaining the rigidity of the titanium about opening 146 reduces the likelihood of a defective or failed connection of feedthrough 150 to housing 132.

Also, because of the low temperatures employed by the brazing process described herein, dimensional changes in housing 132 as a whole are also minimal. The housings of implantable medical devices, such as housing 132 of implantable medical device 130, are typically in two "halves", with a first half including opening 146 and a second half which are later joined together, such as by laser welding, to form complete housing 132. In order to achieve a hermetic seal, the two halves are required to be in close contact with one another during the laser welding process. For example, the dimensional profiles of the two halves of the housing are typically required to be held within a tolerance of +/−0.004". The low-temperatures associated with the brazing process described herein ensure that the dimensional profiles of the housing halves remain within required tolerances.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method of attaching a feedthrough directly to a titanium housing of an implantable medical device, the method comprising:
   providing the housing with a flange forming a recess about an opening through the housing, the opening disposed within the recess;
   positioning the feedthrough directly within the recess so as to form a gap between the flange and an insulator of the feedthrough;
   providing a metalized layer on a surface of the insulator of the feedthrough;
   positioning a braze preform within the recess about the insulator and at least partially outside the gap, the braze preform comprising a biocompatible braze material having a melting point less than a β-transus temperature of the titanium of the housing;

melting the braze preform at a temperature less than the β-transus temperature of the titanium of the housing such that the melted braze material is drawn into and fills the gap via capillary action;

cooling the braze material to form a braze joint which bonds the insulator directly to the housing without an intervening ferrule or other structure and hermetically seals the opening;

wherein positioning the feedthrough within the recess to form the gap comprises positioning such that the gap has a distance in the range of 10-50 μm in order to optimize the capillary action of the braze.

2. The method of claim 1, including forming the braze preform from a gold alloy.

3. The method of claim 2, wherein the gold alloy consists of gold and germanium.

4. The method of claim 2, wherein the gold alloy consists of gold and indium.

5. The method of claim 2, wherein the gold alloy consists of gold, silver, platinum, and zinc.

6. The method of claim 2, wherein the gold alloy consists of gold, silver, platinum, copper, and zinc.

7. The method of claim 1, wherein melting the braze preform includes heating the braze preform to a temperature not exceeding 870° C.

8. The method of claim 1, wherein melting the braze preform includes heating the braze preform to a temperature not exceeding 710° C.

9. The method of claim 1, wherein the method of attaching the feedthrough directly to the titanium housing is characterized by never raising the temperature above the β-transus temperature of the titanium of the housing.

10. The method of claim 1, wherein melting the braze preform includes heating the braze preform to a temperature not exceeding 361° C.

11. The method of claim 1, including metallizing a surface of the insulator to which the braze joint is bonded prior to positioning the feedthrough within the recess.

12. A method of attaching a feedthrough to a titanium housing of an implantable medical device, the method comprising:

providing the housing with a flange defining a recess about an opening through the housing;

positioning the feedthrough within the recess so as to form a gap between the flange and an insulator of the feedthrough;

providing a metalized layer on a surface of the insulator of the feedthrough;

melting a braze material comprising a biocompatible gold alloy having a melting temperature less than a β-transus temperature of the titanium of the housing, and at least partially positioned outside the gap in order to fill at least the gap via capillary action and thereby form a braze joint which bonds the insulator directly to the housing without an intervening ferrule or other structure and hermetically seals the opening, including melting the braze material at a temperature less than the β-transus temperature of the titanium of the housing and for a duration that limits grain growth of the titanium of the housing, within 0.25 inches of the opening, to a grain size not exceeding 150 um;

wherein positioning the feedthrough within the recess to form the gap comprises positioning such that the gap has a distance in the range of 10-50 μm in order to optimize the capillary action of the braze.

13. The method of claim 1, wherein the recess includes an upper portion and a lower portion and positioning the braze preform in the recess further comprises positioning the braze preform in the upper portion and melting the braze preform further comprises melting such that the melted braze material is drawn into the lower portion via capillary action.

14. The method of claim 1, wherein positioning the feedthrough directly within the recess further comprises providing a support element under the feedthrough positioned to support the feedthrough within the recess of the housing and to maintain the gap between the flange and insulator as the braze is drawn into the gap.

* * * * *